United States Patent
Seidmann et al.

[19]

[11] Patent Number: 5,970,795

[45] Date of Patent: Oct. 26, 1999

[54] APPARATUS AND METHOD FOR TESTING ATTENUATION OF IN-USE INSERT HEARING PROTECTORS

[75] Inventors: Michael F. Seidmann, Kenner; Roger P. Juneau, Destrehan, both of La.; Juan H. Sanchez, Springdale, Ark.; Gregory R. Siegle, Kenner, La.

[73] Assignee: Sound Technologies, Inc., Kenner, La.

[21] Appl. No.: 08/908,256

[22] Filed: Aug. 7, 1997

Related U.S. Application Data

[63] Continuation-in-part of application No. 08/338,846, Nov. 14, 1994, Pat. No. 5,757,930
[60] Provisional application No. 60/023,544, Aug. 7, 1996.

[51] Int. Cl.⁶ ........................................................ A61B 5/12
[52] U.S. Cl. .............................. 73/585; 181/135; 381/60; 381/72
[58] Field of Search ................................ 73/585; 381/58, 381/60, 72; 181/130, 135; 128/867

[56] References Cited

U.S. PATENT DOCUMENTS

| | | | |
|---|---|---|---|
| 4,807,612 | 2/1989 | Carlson | 128/868 |
| 5,074,375 | 12/1991 | Grozil | 181/135 |
| 5,333,622 | 8/1994 | Casali et al. | 128/864 |
| 5,757,930 | 5/1998 | Seidemann et al. | 381/60 |

*Primary Examiner*—Hezron Williams
*Assistant Examiner*—Richard A. Moller
*Attorney, Agent, or Firm*—Garvey, Smith, Nebrbass & Doody, L.L.C.

[57] ABSTRACT

The system is designed for the purpose of providing a means of conducting objective assessment of the actual or "real world" attenuation which is provided by insert-type hearing protection (IHP) devices. A device is constructed to serve as the input device to any commercially available noise dosimetry instrument or sound level measuring device. A miniature microphone is mounted on, or embedded in the proximal surface of the IHP which is to be inserted in the ear or upon the ear of the user. The miniature microphone is hard wired to a miniature jack which is mounted on, or embedded in, the distal surface of the IFP device. A cable connects to the jack on the outside of the IHP device and to the input of the noise dosimetry instrument or sound level measurement device. Thereby, when the IHP device containing the above is used, the dosimetry or sound level measurement instrument conducts assessments of actual sound levels to which the hearing mechanism is exposed when IHP devices are in use. In that manner, objective assessment of IHP device effectiveness is accomplished, allowing the ability to obtain experienced (real world) vs. non-experienced (laboratory) data. Furthermore, inter-subject and intra-subject variability as well as intra-IHP and inter-IHP variability data can be collected with the use of this device and method. This device and method also eliminate the need for any audiometric equipment necessary for the prior art assessment of the effectiveness of IHPs in general. In a preferred embodiment, the microphone and jack are mounted in a tube which is then inserted in the IHP. A similar tube, without the microphone and jack, can be used in IHPs actually worn for protection to replicate in field use conditions the field test conditions.

20 Claims, 5 Drawing Sheets

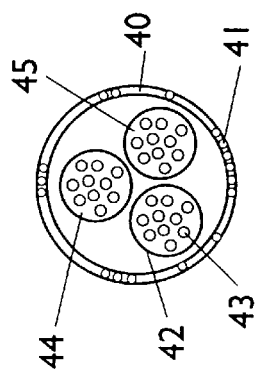
FIG. 2.A
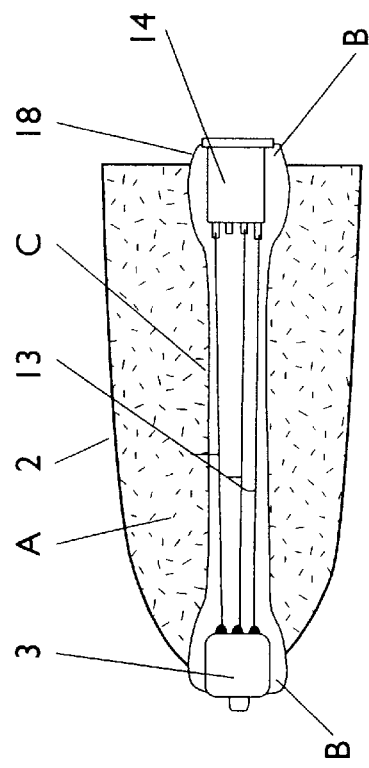
FIG. 2
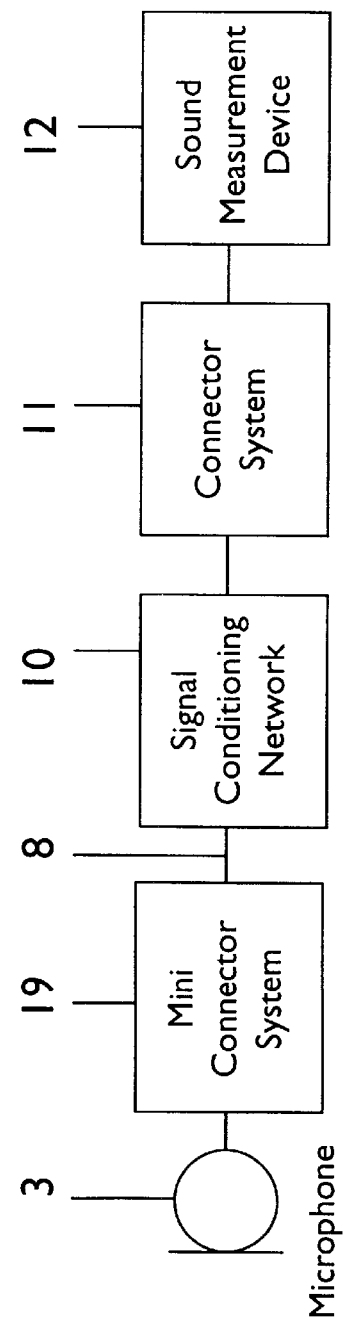
FIG. 3

APPARATUS AND METHOD FOR TESTING ATTENUATION OF IN-USE INSERT HEARING PROTECTORS

CROSS REFERENCE TO RELATED APPLICATIONS

This is a continuation-in-part of co-pending U.S. patent application Ser. No. 08/338,846, filed Nov. 14, 1994, now U.S. Pat. No. 5,757,930, which is incorporated herein by reference.

Priority of U.S. Provisional Patent Application Ser. No. 60/023,544, filed Aug. 7, 1996, incorporated herein by reference, is hereby claimed.

BACKGROUND OF THE INVENTION

1. Field of the Invention

The present invention relates to hearing protection devices. More particularly, the present invention relates to a system and method for testing hearing protection devices in the field to determine their effectiveness as actually used, not as theoretically used.

2. General Background of the Invention

Approximately nine million workers in the United States are exposed to potentially hazardous noise levels in the workplace.

Federal regulation of occupational noise exposure levels (OSHA: CFR 1910.95) has been in place for almost three decades. That regulation provides for use of hearing protection devices in numerous instances of exposure to potentially hazardous levels of workplace noise in order to prevent occupational noise-induced hearing loss. Manufacturers of hearing protection devices are required to label products in terms of noise reduction capability according to the procedures promulgated by the Environmental Protection Agency. That specification is designated as the Noise Reduction Rating (NRR). The method used to calculate the NRR is a laboratory procedure. For more than ten years, scientific research has extensively and consistently demonstrated that the NRR in no way accurately represents the actual, "real world" attenuation of workplace noise which is provided by hearing protection devices. Numerous variables, such as individual fit, insertion or application technique, training, etc., affect the "real world" attenuation provided by hearing protectors. As a result, several computational procedures have been proposed in the scientific literature (such as derating the NRR by 7 dB or by 50%) in an attempt to render a modification of the NRR a more realistic estimate of the actual protection provided. However, all such techniques remain computational, and do not provide a means of objectively measuring the actual level of workplace noise which penetrates the hearing protection device and reaches the worker's hearing mechanism, possibly causing irreversible hearing loss.

U.S. Pat. No. 3,729,598 to Tegt et al. describes a system for measuring the effectiveness of the sound attenuating function of an earphone sound attenuation cover by employing the earphone transducer as a microphone and measuring the noise level with the cover on and with the cover removed, the difference being interpreted as the acoustic attenuation provided by the ear cover.

U.S. Pat. No. 4,020,298 to Epley et al. describes a portable device primarily for use in determining the effectiveness of various personal hearing protectors in attenuating hazardous noise. This is a subjective method whereby hearing tests are conducted using either threshold data in quiet or supra-threshold data in the presence of noise with the protection in place and compared to the open ear (protector out of ear) to establish an audiometric test differential corresponding to the level of protector performance.

U.S. Pat. No. 3,968,334 to Padilla describes a subjective method and apparatus for audiometrically testing the effectiveness and fitting of insert-type hearing protective devices. Each ear is enclosed under an earmuff which allows the pinna to be free of physical contact so as not to distort the ear canal in which the ear plug is inserted. The muff is equipped with an earphone to transmit audiometric signals. The series of transmitted signals are repeated both without and with ear plugs installed in the ears to obtain the relative difference between the two hearing thresholds.

U.S. Pat. No. 5,044,373 to Northeved et al. describes a method of measuring sound pressure levels in the auditory canal of a person in connection with the fitting of a hearing aid. The invention requires two microphones, one for calibration and one connected to a probe tube of known acoustic characteristics. An objective differentiation between the calibration microphone and the probe microphone yield an end result equal to the respective gain or attenuation of the hearing aid. Neither microphone is on the medial surface of the hearing aid and further more precise tube placement, relative to the distance from the ear drum to the tube tip, is necessary to ensure measurements are reproducible from test to test on the same subject by different technicians.

U.S. Pat. No. 5,317,273 discloses a hearing protection device evaluation apparatus for testing the effectiveness of muff-type hearing protectors. It mentions at column 1, fines 26–31 a method of testing ear plugs using an artificial head in which one microphone is placed "inside the head near the artificial ear drum" and the other is placed outside the muff. U.S. Pat. No. 4,586,194 discloses such an artificial head being used to measure earphones.

U.S. Pat. No. 4,060,701 is similar to U.S. Pat. No. 4,020,298 but only measures effectiveness subjectively.

Other patents which may be of interest include the following:

| | |
|---|---|
| U.S. Pat. No. | 3,697,973 to Stevens et al. |
| U.S. Pat. No. | 3,757,769 to Arguimbau et al. |
| U.S. Pat. No. | 3,906,158 |
| U.S. Pat. No. | 4,024,499 |
| U.S. Pat. No. | 4,029,083 to Baylor |
| U.S. Pat. No. | 4,064,362 |
| U.S. Pat. No. | 4,416,155 |
| U.S. Pat. No. | 4,586,194 to Kohashi et al. |
| U.S. Pat. No. | 4,763,753 to Killion |
| U.S. Pat. No. | 4,781,196 to Killion |
| U.S. Pat. No. | 4,813,430 to Hecox et al. |
| U.S. Pat. No. | 4,852,683 to Killion |
| U.S. Pat. No. | 4,966,160 to Birck et al. |
| U.S. Pat. No. | 5,113,967 to Killion et al. |

Whether the failure of a hearing protection device to adequately protect a worker is due to a defective device or improper placement of a hearing protection device in the worker's ear, the potential result can be the same— otherwise preventable noise-induced hearing loss.

BRIEF SUMMARY OF THE INVENTION

The present invention is a method and device which allows objective testing of plug-type hearing protection devices in an actual human ear.

Such objective measurement will provide employers with the ability to assess in-situ the actual levels of noise sustained by employees, and thereby, a mechanism to more realistically reduce or prevent occupational noise-induced hearing loss. In turn, the reduction of the incidence of occupational noise-induced hearing loss will reduce the number of compensation claims filed against employers for such impairments, and thereby should reduce the cost of worker's compensation insurance. Ultimately, such cost containment associated with production should reduce consumer costs of products.

An inexpensive input device and method are provided for in-situ testing and objective measurement of the noise reduction provided by insert-type hearing protection devices. This invention serves as an input device to standard, commercially available sound measuring instruments (sound level meters and noise dosimeters).

In one embodiment of the invention, the apparatus consists of a miniature microphone mounted on the end of a hearing protector which is closest to the wearer's eardrum. The miniature microphone is connected to a jack on the outside surface of the hearing protection device. A cable is used which plugs into the jack on the hearing protection device on one end, and terminates in a signal conditioning stage and plug on the opposite end. The terminal plug connects to a commercially available sound level meter or noise dosimeter.

The device is to be used in the workplace while performing actual daily work operations. By using the device for a representative period of work time, employers will readily be able to assess the adequacy, fit, usage, and effectiveness of the hearing protection device, as well as providing documentation of compliance with federal and state statutes which require not only the mere application of hearing protection devices, but also an assessment of their adequacy relative to the prevention of occupational noise-induced hearing loss.

The use of this device significantly expands the scope of measurement of sound level meters and noise dosimeters. Those instruments until now have been able to assess ambient sound conditions in the absence of the use of hearing protection devices. This invention enables sound level meters and noise dosimeters to measure the effect of hearing protection devices upon the ambient noise environmental conditions.

The present invention measures the actual sound level reaching a worker's eardrum when he is wearing a hearing protection device, regardless of why the sound level might differ from the level predicted in advance (i.e., whether the failure of a hearing protection device to reduce the sound level reaching the worker's eardrum is due to a defective device or improper placement of a non-defective device in the worker's ear). If the sound level is higher than an acceptable level, the placement of the hearing protection device can be adjusted and, if that does not result in an acceptably low level of sound reaching the worker's eardrum, different hearing protection devices can be tested until one which works for the worker is chosen.

The present invention is primarily concerned with determining the actual sound level reaching a worker's eardrum in the field, and is secondarily concerned with comparing sound levels with a hearing protection device in place to sound levels without the hearing protection device in place.

In a preferred embodiment of the present invention, an insert hearing protector (IHP) includes either an Alpha or Delta insert which is implanted through the longitudinal axis of the IHP. The Delta insert is a dummy acousto-mechanical equivalent (or approximate acousto-mechanical equivalent) of the Alpha insert. The Alpha insert is an inexpensive input device and method allowing for in-situ testing and objective measurement of the noise reduction provided by this IHP and other hearing protection devices (such as a muff-type hearing protector which might be worn over the ears in addition to this IHP).

The Alpha insert consists of a solid body made up of a miniature microphone, a three-element cable, a mini-socket, and epoxy encapsulant. The microphone is connected to the mini-socket via the three-element cable, then epoxy is used to form a smooth tube-like assembly. The tube-like assembly is then inserted into the hearing protector. A second cable connects the mini-socket to a sound level meter.

The Delta insert comprises a solid body (a tube-like assembly) made up of a three-element wire and the epoxy encapsulant (or, alternatively, a tube filled with epoxy encapsulant). The Delta insert is used in the IHP when the Alpha insert is not used to provide an acoustic plug in the bore in which the Alpha insert normally fits. The Delta insert is made to replicate the acousto-conductive characteristics of the Alpha insert as closely as possible at the frequencies of sound which the IHP is designed to attenuate. In this way, the sound level measured by the apparatus of the present invention when the Alpha insert is in the IHP is the same which would be reaching the user's ear drum were the Delta insert used instead. Thus, the Alpha IHP helps to accurately predict the sound level which will reach the user's ears when Delta WIPs are used therein.

The present invention comprises an IHP system which includes Alpha IHPs and Delta IHPs, the Alpha IHPs having the Alpha inserts therein, and the Delta IHPs having the Delta inserts therein. At frequencies below 500 Hz, the acoustic impedance of the Alpha insert varies from the acoustic impedance of the Delta insert by not more than 5%, at frequencies of 500 Hz to 1000 Hz, the acoustic impedance of the Alpha insert varies from the acoustic impedance of the Delta insert by not more than 3%, and at frequencies of about 1000 Hz, the acoustic impedance of the Alpha insert varies from the acoustic impedance of the Delta insert by not more than 5%.

At frequencies below 500 Hz, the acoustic impedance of the Alpha IHP varies from the acoustic impedence of the Delta IHP by not more than 5%, at frequencies of 500 Hz to 1000 Hz, the acoustic impedance of the Alpha IHP varies from the acoustic impedance of the Delta IHP by not more than 5%, and at frequencies of about 1000 Hz, the acoustic impedance of the Alpha IHP varies from the acoustic impedance of the Delta IHP by not more than 5%.

An article by Larry Royster entitled "In search of a meaningful measure of hearing protector effectiveness" (Spectrum, Vol. 12, No. 2, May 1995, pp. 1 & 6–13) demonstrates the need for the present invention.

A principal object of this invention is to make use of existing (and future) technology embodied in various forms of sound measurement devices (noise dosimeters and sound level meters) while providing an innovative input device to be used in conjunction with sound measurement devices in order to yield an objective assessment of the "real world" effectiveness of hearing protection devices.

Another important object is to enable the conduction of such measurements in realistic workplace locations rather than in a laboratory.

Still another object is to provide industries and governments with a means to assess the effectiveness of hearing protection programs so that the prevalence of occupational noise-induced hearing loss may be reduced.

Other objects, advantages, and novel features of the invention will become apparent from the following detailed description of the invention when considered in conjunction with the accompanying drawings.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein:

FIG. 2 is a longitudinal cross-sectional view of the modified hearing protector in the Alpha configuration, showing the microphone and mini-socket embedded in the hearing protector;

FIG. 2A is a cross-sectional view of the cable;

FIG. 3 is a block diagram depicting the electrical relationship between the different components, including the microphone, mini-plug and mini-socket assembly, signal conditioning network, and connector to a sound level measuring device;

FIG. 7 is a longitudinal cross-sectional view of the modified hearing protector in the alternative Delta configuration, showing the dummy insert in the hearing protector.

PARTS LIST

Figure 1:
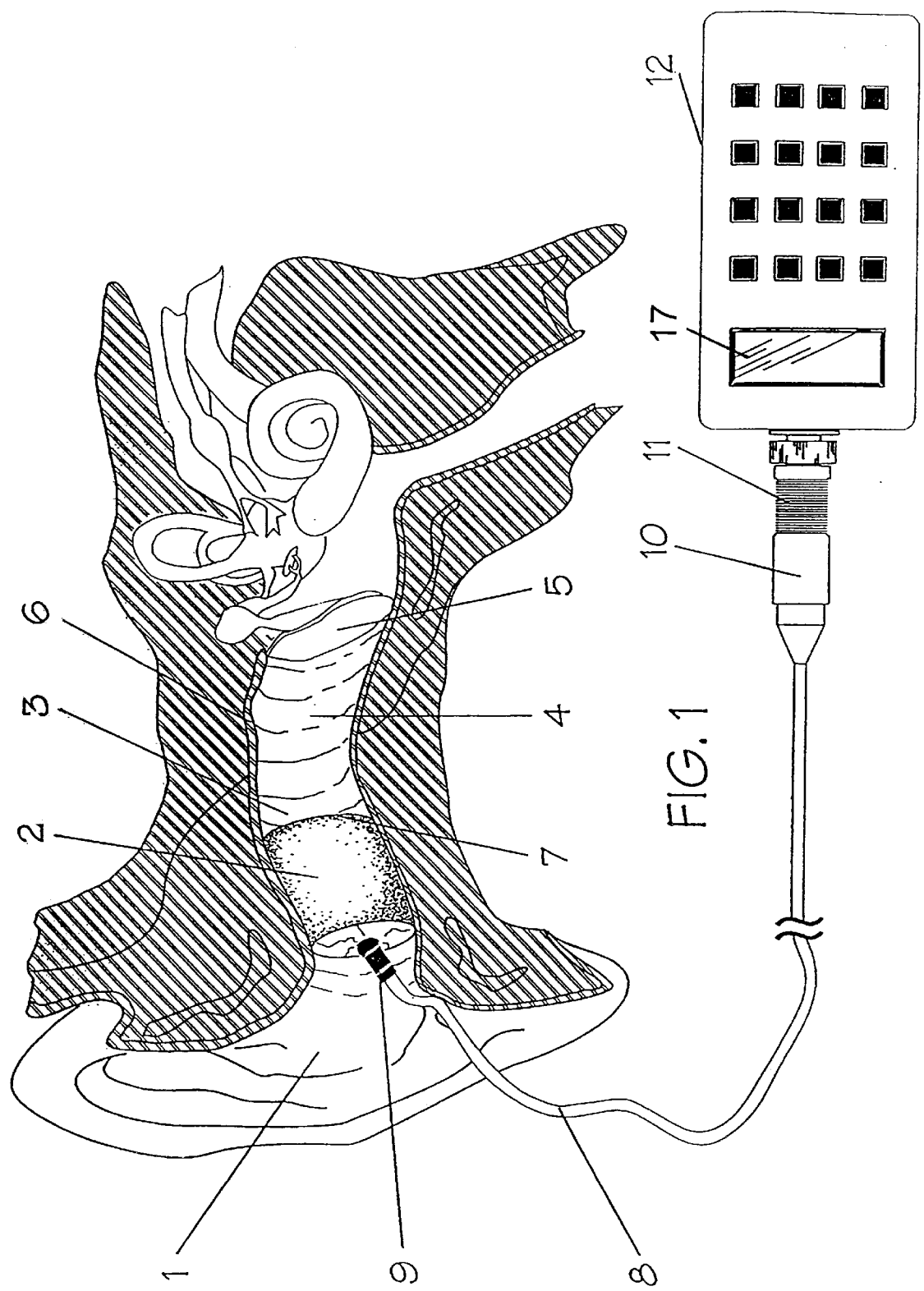
FIG. 1 shows the device in the Alpha configuration as it would be worn in the ear.

The following is a list of suitable parts and materials for the various elements of the preferred embodiment of the present invention.

| | |
|---|---|
| A | IHP body (e.g., sponge or foam material, such as polyvinyl or polyurethane; it could be a modified 3M brand ear plug, part no. 1100) |
| B | epoxy encapsulant (e.g., Esschem brand epoxy) |
| C | hollow tube for containing microphone 3, wires 13, mini-socket 14, and epoxy B (Alpha tube 18) or for containing epoxy B and wires 13 (Delta tube 20) (hollow tube C is preferably the shield of a shielded cable, such as shield 41 of cable 40) |
| 1 | human ear |
| 2 | modified hearing protector (e.g., modified 3M brand ear plug, part no. 1100) with Alpha insert 18 |
| 3 | microphone (e.g., part no. EM 3046 or XD 1335-056 from Knowles of Itasca, Illinois) |
| 4 | air |
| 5 | tympanic membrane (eardrum) |
| 6 | ear canal wall |
| 7 | proximal end of the hearing protector |
| 8 | cable (e.g., three-element covered shielded) |
| 9 | mini-plug (e.g., part no. CS 44-0-10-1-1 from Microtronic A/S of Roskilde, Denmark) |
| 10 | signal conditioning network |
| 11 | connector (e.g., Hirose Elect. Co. brand, model no. SR30-0-10PE-4P) |
| 12 | noise dosimeter or other sound level measurement equipment (e.g., Quest Electronics Dosimeter, Model M-28 or M-27) |
| 13 | wires (e.g., three-conductor with shield from CS connector system from Microtronics U.S. of Chicago, Illinois - part no. 44-0-15-1-1) |
| 14 | mini socket, part no. CS 44-1-020 from Microtronic A/S of Roskilde, Denmark |
| 17 | display of dosimeter 12 |
| 18 | Alpha verifier insert |
| 19 | mini-connector system (made up of plug 9, wires 13, and mini socket 14) |
| 20 | Delta verifier insert |
| 22 | modified hearing protector (e.g., modified 3M brand ear plug, part no. 1100) with Delta insert 20 |
| 30 | alternative Delta verifier insert |
| 30C | hollow tube for containing epoxy B (hollow tube 30C could be Silastic ™ brand silicone tubing, for example) |
| 32 | modified hearing protector (e.g., modified 3M brand ear plug, part no. 1100) with alternative Delta insert 30 |
| 40 | insulated cable (e.g., three-conductor with shield from CS connector system from Microtronics U.S. of Chicago, Illinois - part no. 44-0-15-1-1) |
| 41 | forty strand ground shield |
| 42 | black stranded wire, ten-strand, twenty-gauge, insulated |
| 43 | ten strand conductor (wires 13 could comprise conductors 43) |
| 44 | white stranded wire, ten-strand, twenty-gauge, insulated |
| 45 | red stranded wire, ten-strand, twenty-gauge, insulated |

DETAILED DESCRIPTION OF THE INVENTION

The device of this invention is meant to be inserted in the human ear which is marked as 1 in FIG. 1. The modified hearing protector is depicted as 2. The microphone 3 (see FIG. 2) measures the noise level to which the volume of air 4 (see FIG. 1—defined by the tympanic membrane 5, the canal wall 6, and the proximal end of the hearing protector 7) is exposed. The sound in air volume 4 is converted (transduced) into an electrical signal by the microphone 3, and directed to the cable assembly through a mini-plug 9. The signal travels through the cable 8 and is modified by a signal conditioning network 10 so it can be coupled through the connector 11 to the noise dosimeter or other sound level measurement equipment 12. The modified hearing protector 2 is inserted into the ear 1 exactly in the same manner as the intact hearing protector would, according to the hearing protector manufacturer's instructions.

A cross-sectional view of the hearing protector assembly is shown in FIG. 2. The Alpha insert 18 includes the shield C of a shielded three-conductor cable, a miniature microphone 3, a three-element cable (wires 13), a mini-socket 14, and an epoxy encapsulant B. The microphone 3 is connected to the mini-socket 14 via the three-element cable (wires 13), then epoxy encapsulant B is used to fill the shield C. The Alpha insert 18 is then inserted into the IHP body A to form hearing protector 2. As can be seen in FIGS. 1 and 2, hearing protector 2 is a generally cylindrical plug. A hollow tube (such as tube 30C) could replace shield C if a shielded cable is not used. Shielded cable 40 (see FIG. 2A) could make up shield C and wires 13.

Preferably, the microphone 3 and shielded cable comprising wires 13 and shield C are chosen such that the microphone 3 fits into the shield C. Appropriate combinations include part no. EM 3046 or XD 1335-056 from Knowles of Itasca, Ill. as microphone 3 and three-conductor with shield from CS connector system from Microtronics U.S. of Chicago, Ill.—part no. 44-0-15-1-1 as the shielded cable.

The microphone 3 is embedded in the side 7 of the hearing protector 2 which is inserted first into the ear 1.

The Delta insert 20 comprises the shield C of a shielded 3-conductor cable, wires 13 of the shielded 3-conductor cable, and the epoxy encapsulant B. The Delta insert 20 is preferably used in the IHP A when the Alpha insert 18 is not used to provide an acoustic plug in the bore in which the Alpha insert 18 normally fits. The Delta insert 20 is made to replicate the acousto-conductive characteristics of the Alpha insert 18 as closely as possible at the frequencies of sound which the IHP is designed to attenuate.

An alternative Delta insert 30 is shown in FIG. 7. Alternative Delta insert comprises a hollow tube 30C and the epoxy encapsulant B. The alternative Delta insert 30 is used in the IHP A in a manner similar to that of Delta insert 20. The alternative Delta insert 30 is made to replicate the acousto-conductive characteristics of the Alpha insert 18 as closely as possible at the frequencies of sound which the IHP is designed to attenuate.

The complete Alpha system is depicted in FIG. 3. The sound enters the microphone 3 and is converted to an electrical signal, which is directed to one side of the mini socket 14. The microphone 3 and half of the mini socket 14 are embedded in the distal end of hearing protector 2 (not shown in FIG. 3). The electrical signal then travels through a cable 8 to the signal conditioning network 10 (comprising an amplifier and/or an impedance matching network). This signal conditioning network 10 can comprise active or passive components such as an amplifier, filters, and other discrete components, in order to appropriately couple the signal to the sound level measuring device 12. The signal conditioning network 10 is coupled to the sound level measuring device 12 through a connector system 11 that matches the one used by the sound level measuring device. When the sound measurement device is a Quest Model M-28 Dosimeter, signal conditioning network 10 can advantageously comprise a 127K Ohm resistor.

In order to optimize performance and minimize the standard deviation of the hearing protector's attenuation characteristics, the Alpha insert 18 and Delta insert 20 are made as similar as possible in terms of physical size and hardness.

Figure 4:
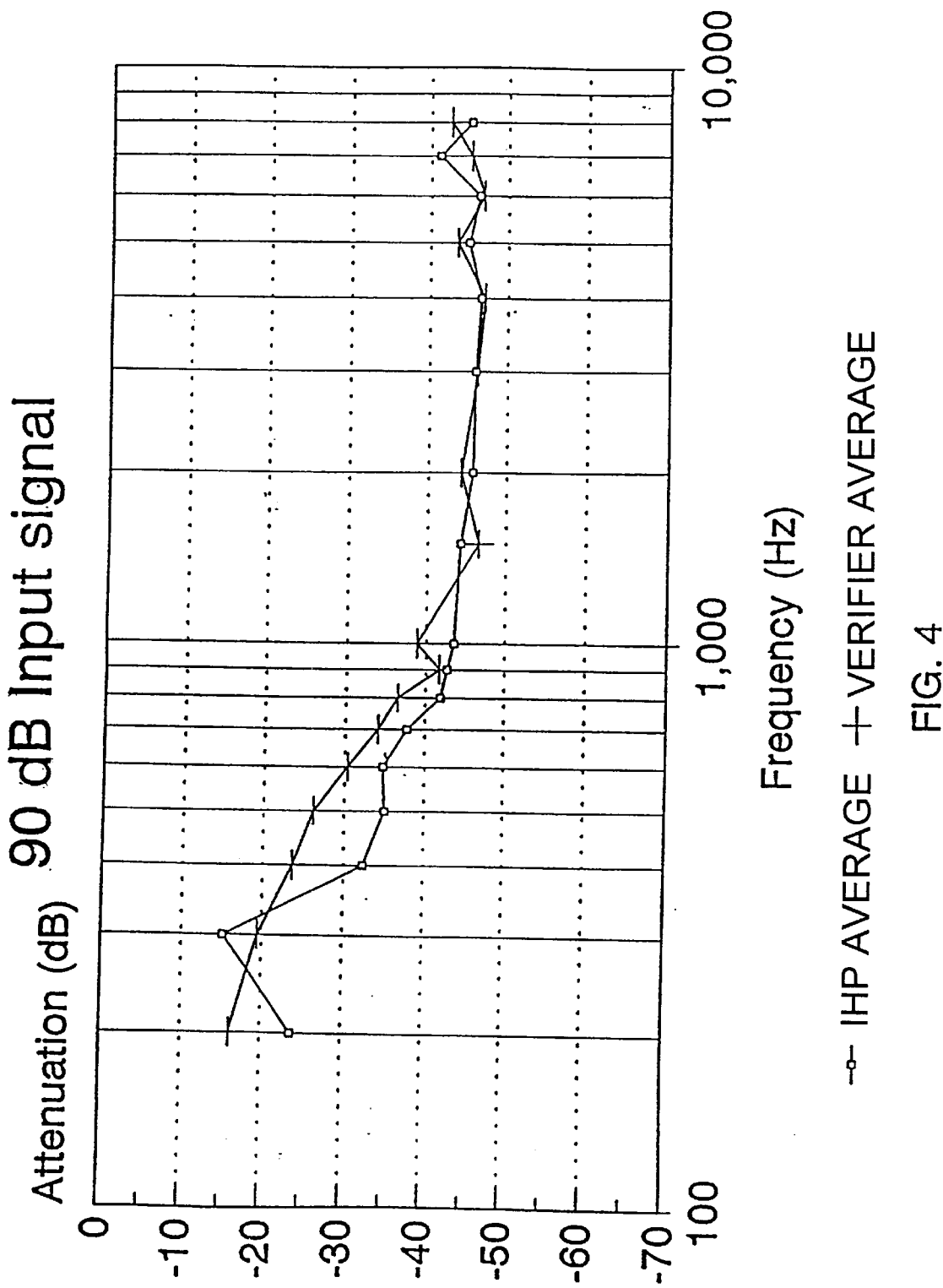
FIG. 4 shows the attenuation characteristics of the device or modified hearing protector, as well as the intact hearing protector.
Figure 5:
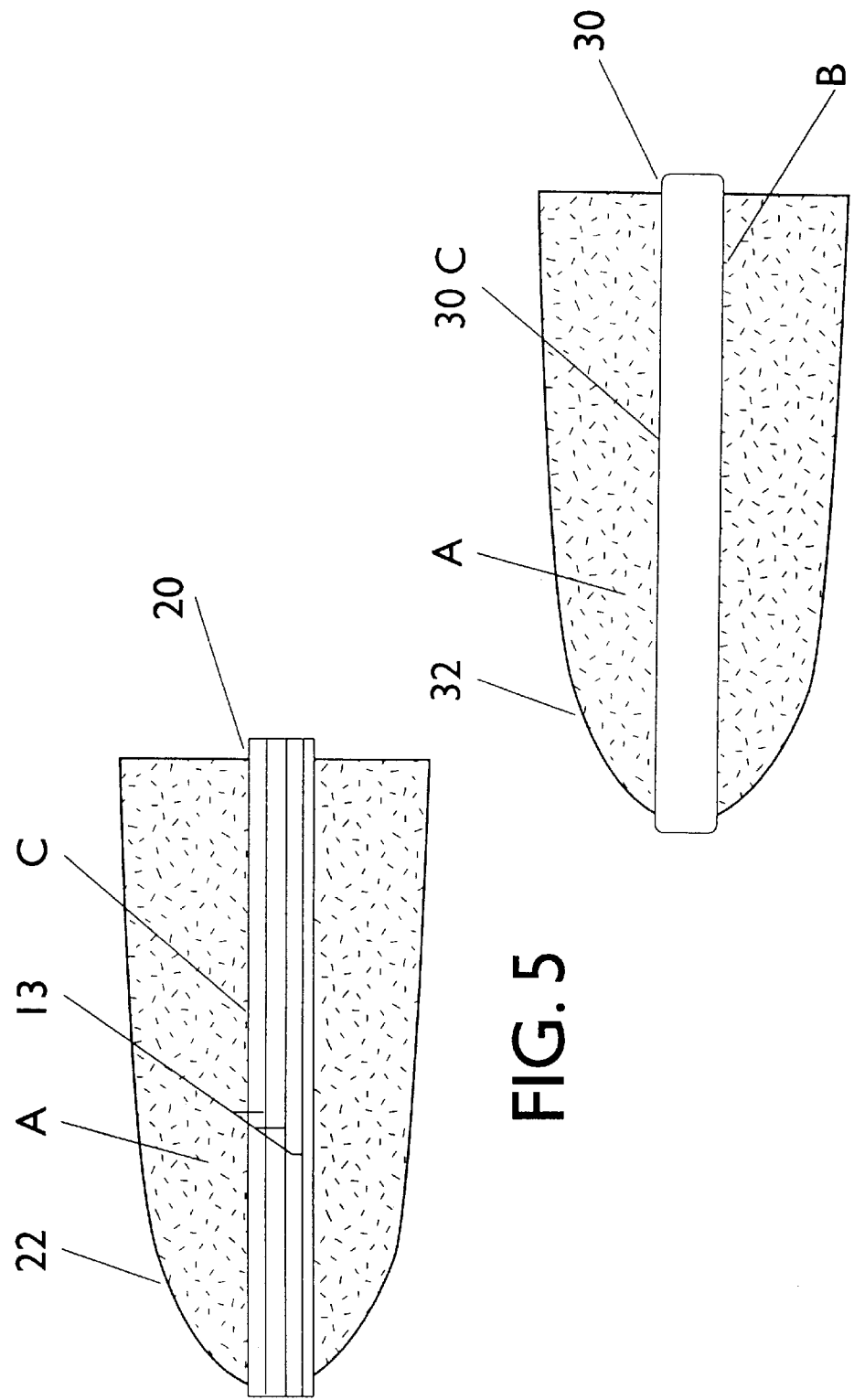
FIG. 5 is a longitudinal cross-sectional view of the modified hearing protector in the Delta configuration, showing the dummy insert in the hearing protector.
Figure 6:
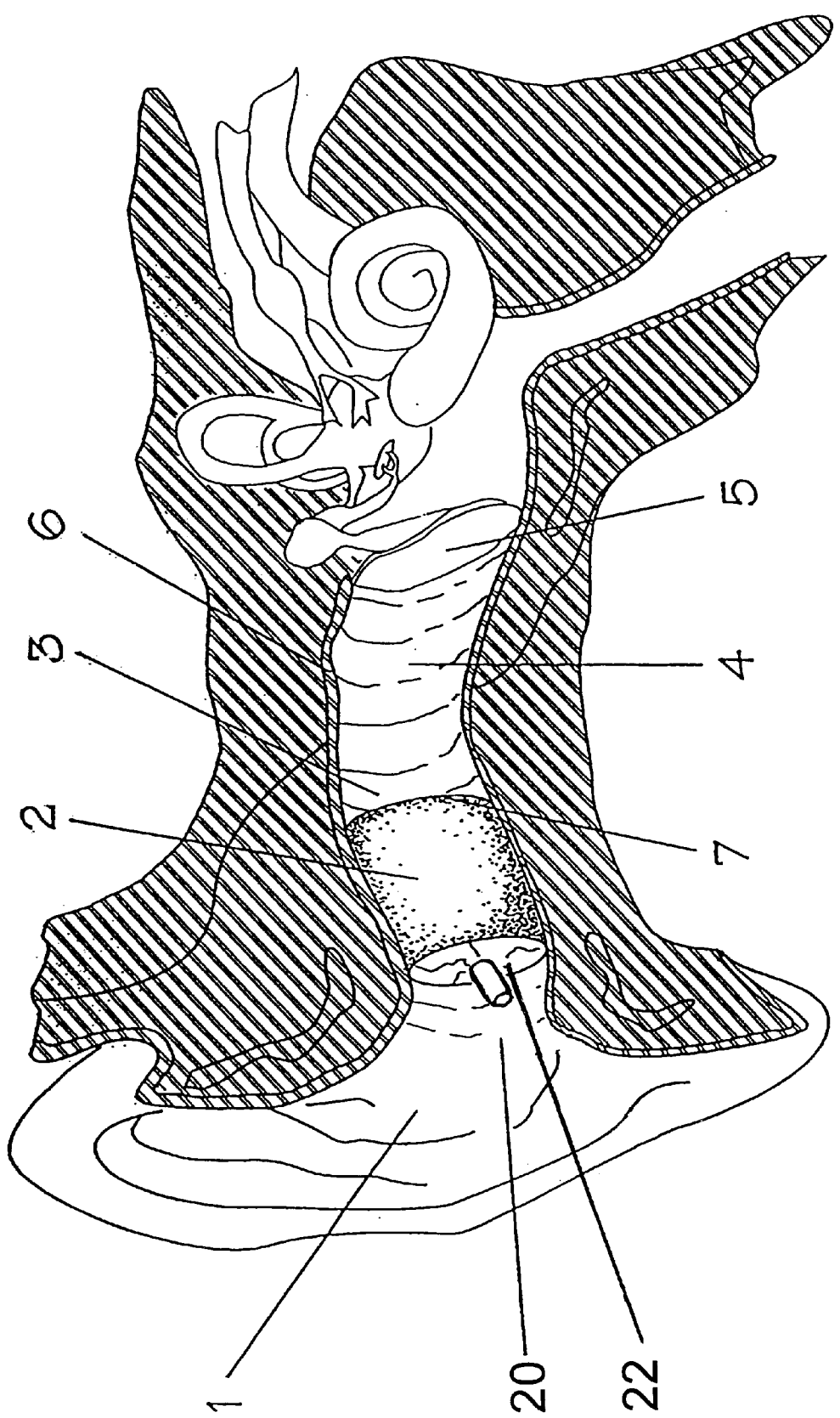
FIG. 6 shows the device in the Delta configuration as it would be worn in the ear.

FIG. 4 shows the attenuation characteristics of the intact hearing protectors and modified hearing protectors when inserts 18 and 20 are not used, and instead minimum-size cavities are made in the hearing protector 2 in order to accommodate the microphone 3 and half of the mini socket 14, as in FIG. 2 of our prior, co-pending patent application. As can be seen in FIG. 4, the IHPs attenuate between about 15 dB and 45 dB of the noise level of a 90 dB input signal. The data is the average for nine intact 3M brand model no. 1100 hearing protectors ("IHP Average") and the average of nine modified 3M brand model no. 1100 hearing protectors ("Verifier Average"). Different hearing protectors were considered with similar NRR ratings. The modifications show that the attenuation of low frequencies (<500 Hz) is reduced by 10 dB, reduced by 5 dB between 500 and 1,000 Hz, and remains unaffected for higher frequencies (>1 kHz). A study will be published in the near future to assess whether or not the differences for the low and mid frequencies are statistically significant and whether or not they affect the accurate measurement of noise levels.

Even though the difference between the modified hearing protectors 2 of FIG. 2 of our prior patent application and unmodified hearing protectors appears to be negligible, it is desirable to have the tested earplug be as similar to the one to be actually used by workers as possible. The present inventors realize that one good way to do so is to form each earplug in such a shape that it does not need to be altered to receive the testing apparatus (microphone 3, mini socket 14, wires 13). In this way, the results of the tests will be most usefull and most accurate for predicting actual attenuation. Thus, it is preferable to form all hearing protectors 2 to be worn by workers where the system of the present invention is used to test the actual attenuation of the hearing protectors in the shape shown in FIG. 2. Thus, there will be no discrepancy or as little discrepency as possible between the tested units and the units which are actually worn by the workers.

Hearing protectors 2 (IHPs A with Alpha inserts 18), hearing protectors 22 (IHPs A with Delta inserts 20), and hearing protectors 32 (IHPs A with alternative Delta inserts 30) attenuate between about 15 dB and 45 dB of the noise level of a 90 dB input signal. The attenuation of relatively low frequencies (300, 400, 500, 600 Hz) differs by about one dB depending upon whether the Alpha insert 18 or the Delta insert 20 is used (slightly better attenuation being obtained with the Delta insert 20), while at mid-range and high frequencies (above 600 Hz), the difference is not detectable.

As can be seen in FIG. 4, the IHPs of the present invention can attenuate at least about 15 dB of the noise level reaching the distal tip of the IHP.

Acoustical performance of the IHPs with Delta inserts 20 more closely resembles acoustical performance of the IHPs with Alpha insert 18 than does the acoustical performance of the IHPs of our prior co-pending patent application which are not modified resemble acoustical performance of the IHPs with the microphone assembly. This is because the Delta inserts 20 have acoustical impedance which is approximately equal to that of the Alpha inserts 18 at frequencies of noise with which IHP body A is designed to be used.

Procedure for Making the Alpha Insert

The Alpha insert 18 is made by first cutting a piece of wire to a length approximately 4 mm longer than the IHP body A. The outer insulation is then stripped off of about 4 of mm the wire, with care being taken not to nick the insulation of the wires 13 inside. The three wires are unbraided. The cloth braid is cut off at the edge of the outer insulation. Then the end 1 mm of the insulation of the inner wires 13 is stripped off The wires 13 are then soldered to the microphone 3. The outer insulation is then removed from the other end of the wire (the end 1 mm). The outer insulation is then moved such that 2 mm of the second end of the wires projects from the outer insulation. The inner wires are prepared as before, and then soldered onto the CS-44 mini-socket 14. The outer insulation is then slid back towards the socket 14 so that it is approximately even on each end. The microphone 3 and socket 14 are then coated with Sicomet/polymer (black) mixture. This must be done quickly for a smooth, even finish.

Procedure for Using the Present Invention

In order to use the present invention, the dosimeter or sound level meter 12 should be calibrated to the microphone 3. A sound calibrator (not shown), such as Quest Electronics brand model no. CA-12B, can be used for this purpose like it would be used for the standard microphone. The present product design of the present invention can advantageously be used with the Quest M-28 Noise Logging Dosimeter commercially available from Quest Electronics of Oconomowoc, Wis., or other similar device. The signal conditioning network 10 featured in the adapter cable 8 ensures that the signal level from the output of microphone 3 is at the level necessary for the dosimeter or sound level meter 12 to work accurately.

The plug 2 should be compressed to its minimum diameter in order to insert it in the calibrator's coupler. With the present invention connected to the dosimeter 12 through the adapter cable 8, and both the dosimeter 12 and calibrator (not shown) turned on, the calibration potentiometer on the dosimeter must be adjusted until a reading matches the output level of the calibrator.

After the dosimeter 12 has been calibrated, the present invention is ready for use. The plug 2 should be compressed into its smallest diameter for insertion into the ear 1. It should be inserted like a regular hearing protector would be inserted. After it is inserted, the present invention can be used to collect noise measurement data from within the ear 1, thus allowing for measurements of noise exposure at the tympanic membrane end 7 of the hearing protector.

The present invention is the only device known to the present inventors which objectively measures the sound level in the ear canal of a user between the user's eardrum and a hearing protection device being worn by the user. Although in the drawings the objective measurement occurs in the ear canal of a user between the user's eardrum and an insert-type hearing protection device being worn by the user, the objective measurement could as well occur in the ear canal of a user between the user's eardrum and a muff-type hearing protection device being worn by the user. In e event, one would learn the sound level at the most important location for hearing protection —in the ear canal of a user adjacent the user's eardrum. Thus, the device of the present invention for measuring sound level can be used with any available insert, semi-aural, or muff-type, hearing protector. It operates electroacoustically.

In some cases, epoxy B can be omitted with little effect on the acoustical properties of the inserts 18 and 20.

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

We claim:

1. A device for measuring noise level from a proximal tip of an insert-type hearing protector (IHP) placed in a user's ear canal, the user having a tympanic membrane, wherein the proximal tip of the IHP faces the user's tympanic membrane and the IHP has a distal tip, and there is an airspace between the proximal tip of the IHP and the tympanic membrane, the device comprising:

a. an IHP which can attenuate at least about 15 dB of the noise level reaching the distal tip of the IHP;

b. a microphone placed at the proximal tip of the IHP for transmitting sound from within the airspace between the proximal tip of the IHP and the tympanic membrane;

c. electronic coupling means for electronically coupling the microphone to a sound measuring means.

2. An objective method of measuring the sound attenuating effectiveness of an insert-type hearing protector (IHP), comprising the steps of:

a) providing a device for measuring noise level from a proximal tip of an IHP placed in a user's ear canal, the user having a tympanic membrane, wherein the proximal tip of the IHP faces the user's tympanic membrane and the IHP has a distal tip, and there is an airspace between the proximal tip of the IHP and the tympanic membrane, the device comprising:

(i) an IHP which can attenuate at least about 15 dB of the noise level reaching the distal tip of the IHP;

(ii) a microphone placed at the proximal tip of the IHP for transmitting sound from within the airspace between the proximal tip of the IHP and the tympanic membrane; and (iii) electronic coupling means for electronically coupling the microphone to a sound measuring means;

b) calibrating the sound measuring means using the microphone; and c) using the device to measure noise level within the ear canal of the user, the ear canal having the IHP placed therein.

3. The method of claim 2, further comprising the step of selecting an appropriate type and size of IHP to be worn by an employee at the worksite, based on fit and IHP performance in the employee's ear.

4. The method of claim 2, further comprising the step of qualifying and quantifying the amount of protection that an IHP can provide to employees at their respective worksites.

5. The method of claim 2, wherein laboratory-generated noise is used as a sound source.

6. The method of claim 2, further comprising the step of testing the effectiveness of an IHP on a pre-determined number of users in order to obtain a better estimate of the IHP's ideal NRR, as well as the "real world" NRR.

7. The method of claim 2, wherein pure tones are used as a sound source.

8. The method of claim 2 wherein such method provides a means of objectively qualifying and quantifying an employee's ability to use a particular IHP, comprising the additional steps of:

a. the employee inserting the HIP as he usually wears an IHP for hearing protection;

b. the employee being exposed to the noise environment needed for the test;

c. the amount of protection provided by the IHP as inserted by the employee being compared to the manufacturer determined NRR rating of the IHP and by comparison it can be determined whether or not the employee is wearing the IHP in an effective manner to attenuate noise, and whether or not the employee needs further training in the proper use and insertion of the IHP or whether a more appropriate type or size of IHP should be recommended.

9. The method of claim 2, wherein worksite ambient noise is used as a sound source.

10. The device of claim 1, wherein the sound measuring means comprises a dosimeter or sound level meter.

11. The device of claim 1, wherein the electronic coupling means includes:
   a cable assembly and a connector,
   the connector being at the distal tip of the IHP for mechanically and electrically coupling the microphone to the cable assembly,
   the cable assembly electronically coupling the connector to the sound measuring means.

12. Apparatus including:
   an insert hearing protector (IHP) for placement in an ear canal of a user to help reduce noise which reaches the user's eardrum, comprising a generally cylindrical plug made of a relatively soft, pliable material, the plug having a first end portion for placement in the ear canal, a second end portion which projects out of the ear canal when the plug is properly placed in a user's ear canal, and a proximal tip on the first end portion;
   a first receptacle in the first end portion of the plug for receiving a microphone;
   a microphone placed at the proximal tip of the IHP for transmitting sound from within the airspace between the proximal tip of the IHP and the tympanic membrane; and
   electronic coupling means for electronically coupling the microphone to a sound measuring means.

13. Apparatus for measuring the effectiveness of an IHP having a first end for placement proximal a user's tympanic membrane when the IHP is properly placed in a human ear and a second end which is distal from the tympanic membrane when the IHP is properly placed in a human ear, comprising:
   a microphone for placement adjacent the first end of the IHP;
   transmission means for transmitting a signal from the microphone to a dosimeter or sound level meter.

14. An insert-type hearing protector (IHP) system which includes:
   Alpha IHPs and Delta IHPs, the Alpha IHPs having Alpha inserts therein, and the Delta IHPs having Delta inserts therein, each IHP having a proximal tip which can be placed in a user's ear canal, the user having a tympanic membrane, wherein the proximal tip of the IHP faces the user's tympanic membrane when the IHP is properly worn by the user and the IHP has a distal tip, and there is an airspace between the proximal tip of the IHP and the tympanic membrane when the IHP is worn properly, each IHP having means for attenuating at least about 15 dB of the noise level reaching the distal tip of the IHP;
   each IHP having a central bore for receiving an insert;
   each Alpha insert including a microphone at a first end thereof, wherein during proper use of the Alpha IHP the microphone is placed at the proximal tip of the IHP for transmitting sound from within the airspace between the proximal tip of the IHP and the tympanic membrane;
   electronic coupling means for electronically coupling the microphone to a sound measuring means;
   the Delta inserts having a size and shape approximately corresponding to the size and shape of the Alpha inserts;
   wherein at frequencies below 500 Hz, the acoustic impedance of the Alpha IHP varies from the acoustic impedance of the Delta IHP by not more than 5%, at frequencies of 500 Hz. to 1000 Hz, the acoustic impedance of the Alpha IHP varies from the acoustic impedance of the Delta IHP by not more than 5%, and at frequencies of above 1000 Hz, the acoustic impedance of the Alpha IHP varies from the acoustic impedance of the Delta IHP by not more than 5%.

15. A Delta insert-type hearing protector (IHP) for use in an IHP system which includes:
   Alpha IHPs and Delta IHPs, the Alpha IHPs having Alpha inserts therein, and the Delta IHPs having Delta inserts therein, each IHP having a proximal tip which can be placed in a user's ear canal, the user having a tympanic membrane, wherein the proximal tip of the IHP faces the user's tympanic membrane when the IHP is properly worn by the user and the IHP has a distal tip, and there is an airspace between the proximal tip of the IHP and the tympanic membrane when the IHP is worn properly, each IHP having means for attenuating at least about 15 dB of the noise level reaching the distal tip of the IHP;
   each IHP having a central bore for receiving an insert;
   each Alpha insert including a microphone at a first end thereof, wherein during proper use of the Alpha IHP the microphone is placed at the proximal tip of the IHP for transmitting sound from within the airspace between the proximal tip of the IHP and the tympanic membrane;
   electronic coupling means for electronically coupling the microphone to a sound measuring means;
   the Delta inserts having a size and shape approximately corresponding to the size and shape of the Alpha inserts;
   wherein at frequencies below 500 Hz, the acoustic impedance of the Alpha IHP varies from the acoustic impedance of the Delta IHP by not more than 5%, at frequencies of 500 Hz to 1000 Hz, the acoustic impedance of the Alpha IHP varies from the acoustic impedance of the Delta IHP by not more than 5%, and at frequencies of above 1000 Hz, the acoustic impedance of the Alpha IHP varies from the acoustic impedance of the Delta IHP by not more than 5%.

16. An insert-type hearing protector (IHP) system which includes:
   Alpha IHPs and Delta IHPs, the Alpha IHPs having Alpha inserts therein, and the Delta IHPs having Delta inserts therein, each IHP having a proximal tip which can be placed in a user's ear canal, the user having a tympanic membrane, wherein the proximal tip of the IHP faces the user's tympanic membrane when the IHP is properly worn by the user and the IHP has a distal tip, and there is an airspace between the proximal tip of the IHP and the tympanic membrane when the IHP is worn properly, each IHP having means for attenuating at least about 15 dB of the noise level reaching the distal tip of the IHP;
   each IHP having a central bore for receiving an insert;
   each Alpha insert including a microphone at a first end thereof, wherein during proper use of the Alpha IHP the microphone is placed at the proximal tip of the IHP for transmitting sound from within the airspace between the proximal tip of the IHP and the tympanic membrane;

electronic coupling means for electronically coupling the microphone to a sound measuring means;

the Delta inserts having a size and shape approximately corresponding to the size and shape of the Alpha inserts;

wherein at frequencies below 500 Hz, the acoustic impedance of the Alpha insert varies from the acoustic impedance of the Delta insert by not more than 5%, at frequencies of 500 Hz to 1000 Hz, the acoustic impedance of the Alpha insert varies from the acoustic impedance of the Delta insert by not more than 3%, and at frequencies of above 1000 Hz, the acoustic impedance of the Alpha insert varies from the acoustic impedance of the Delta insert by not more than 5%.

17. An objective method of measuring the sound attenuating effectiveness of an insert-type hearing protector (IHP) placed in a user's ear canal, the user having a tympanic membrane, wherein the IHP has a proximal tip which faces the user's tympanic membrane and the IHP has a distal tip, and there is an airspace between the proximal tip of the IHP and the tympanic membrane, comprising the steps of:

(a) placing a microphone at the proximal tip of the IHP for transmitting sound from within the airspace between the proximal tip of the IHP and the tympanic membrane;

(b) electronically coupling the microphone to a sound measuring means; and (c) measuring noise level within the ear canal of the user by measuring the sound transmitted from the microphone to the sound measuring means.

18. The method of claim 17, wherein the IHP can attenuate at least about 15 dB of the noise level reaching the distal tip of the IHP.

19. The method of claim 17, further comprising the step of calibrating the sound measuring means with the microphone.

20. The method of claim 17, wherein the sound measuring means comprises a dosimeter or sound level meter.

* * * * *